128/660

United States Patent [19]

Hassler et al.

[11] Patent Number: 4,478,084
[45] Date of Patent: Oct. 23, 1984

[54] ULTRASOUND TOMOGRAPHY DEVICE

[75] Inventors: Dieter Hassler, Uttenreuth; Elmar Trautenberg, Fuerth-Stadeln, both of Fed. Rep. of Germany

[73] Assignee: Siemens AG, Berlin and Munich, Fed. Rep. of Germany

[21] Appl. No.: 503,438

[22] Filed: Jun. 13, 1983

[30] Foreign Application Priority Data

Jun. 30, 1982 [DE] Fed. Rep. of Germany ....... 3224412

[51] Int. Cl.³ ............................................. G01N 29/00
[52] U.S. Cl. ......................................... 73/620; 73/612; 73/621; 128/660
[58] Field of Search .................. 73/597, 599, 607, 612, 73/614, 615, 618, 620, 621, 625, 626, 628, 641; 128/660

[56] References Cited

U.S. PATENT DOCUMENTS

| 3,990,300 | 11/1976 | Kossoff | 73/626 |
| 4,105,018 | 8/1978 | Greenleaf et al. | 73/597 |
| 4,245,511 | 1/1981 | Soldner | 73/625 |
| 4,272,991 | 6/1981 | Cribbs | 73/621 |

FOREIGN PATENT DOCUMENTS 1316549 5/1973 United Kingdom .

OTHER PUBLICATIONS

"Fifth International Symposium on Ultrasonic Imaging and Tissue Characterization and Second International Symposium on Ultrasonic Materials Characterization", Jun. 1-6, 1980, p. 7.
Ultrasonic Imaging I, pp. 154–184 (1979) by Stephen J. Norton and Melvin Linzer.

Primary Examiner—Stephen A. Kreitman
Attorney, Agent, or Firm—Karl F. Milde, Jr.

[57] ABSTRACT

An ultrasound tomography device for scanning an object under examination from a plurality of directions. Coronal slice images of the plane or planes near or at the female breast wall are obtained. A sagittal scanner is used to obtain numerous small sectional oblique views of the slice to be viewed. A full image of the coronal slice plane is reconstructed through section by section combination of the images obtained from the several small sagittal sections. By providing the sagittal scanner with a scanning motion as well as with translational mobility a full composite view is provided.

8 Claims, 5 Drawing Figures

ULTRASOUND TOMOGRAPHY DEVICE

BACKGROUND OF THE INVENTION

The invention relates to an ultrasound tomography device in accordance with the characteristics and main concepts set forth below.

An ultrasound tomography device for transmission tomography (UCTT) is, for example, known through U.S. Pat. No. 4,105,018. That patent describes an individual ultrasound transmitter, which includes several narrow transmission converter elements on a concave-shaped radiation surface, and which generates a fanlike expanding field of ultrasound waves. A convex-shaped large surfaced ultrasound array with a number of individual reception converter elements is used as an ultrasound receiver. The configuration of the ultrasound transmitter and ultrasound receiver array can be rotated around an object to be examined. In this way tomographical slices derived from a plurality of different perspectives are provided. As with the X-ray computer tomography, the intensities at the intersections of the ultrasound waves in the different perspectives are computed and used for the subsequent calculation of a tomography slice. With respect to reflection tomography (UCRT), on the other hand, ultrasound tomography devices are described in the essay "Resolution and Image Quality By Ultrasonic Echo Tomography: Experimental Approach" by E. Hundt, G. Maderlechner, E. Kronmueller and E. Trautenberg from the "Fifth International Symposium on Ultrasonic Imaging and Tissue Characterization And Second International Symposium on Ultrasonic Materials Characterization", June 1-6, 1980, page 7, and in the essay "Ultrasonic Reflectivity Tomography: Reconstruction with Circular Transducer Arrays" by Stephen J. Norton and Melvin Linzer from "Ultrasonic Imaging 1", 1979, pages 154–184.

Similarly, difficulties are encountered with the ultrasound scanning device disclosed in U.S. Pat. No. 3,990,300, which generates sagittal image slices by employing a number of individual sector scanners. With this system, the individual sector scanners are arranged on an arc segment. This arc segment can be moved by means of a carriage in horizontal or vertical direction relative to the object to be examined. Rotation around the object to be examined is not a feature of the disclosed device.

SUMMARY OF THE INVENTION

It is an objective of this invention to disclose an ultrasound tomography device which can provide, in addition to sagittal slice images, coronal slice images without an extensive additional technical investment. In particular, the present invention will provide coronal slice images of tissue situated close to the breast wall.

By means of a time gate circuit, the invention enables a section by section reconstruction of a coronal slice image close to the breast wall from a plurality of sagittal slices. Other, parallel coronal slice images can be obtained as well. This is accomplished by controlling the set gate times at the time gate circuit as required by controlling the distance of the scanning system to the breast wall. Equally, where necessary, only sagittal slice images can be generated. Therefore, with a minor hardware investment an optimal variety of application possibilities has been provided.

Other features and advantages of the invention will be apparent from the following description of the preferred embodiments, and from the claims.

For a full understanding of the present invention, reference should now be made to the following detailed description of the preferred embodiments of the invention and to the accompanying drawings.

DETAILED DESCRIPTION

Figure 1:
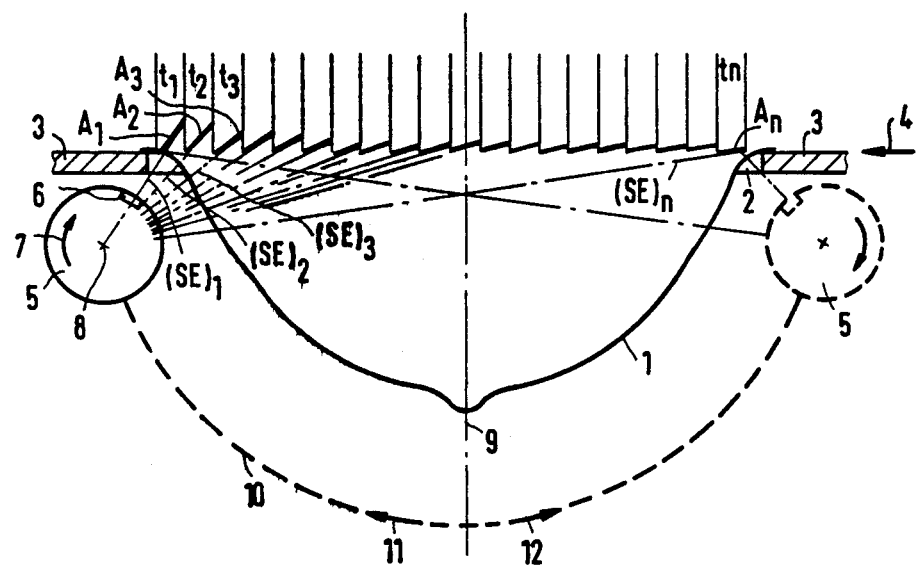
FIG. 1 shows a first sample embodiment of the invention.

In FIG. 1 a female breast 1 extends as the object to be examined through the application opening 2 of a board 3 (which is part of a patient table on which the patient has been placed). Arrow 4, when extended, indicates a coronal slice plane close to the breast wall. An ultrasound transmitting/receiving system 5 is to provide a coronal slice image of tissue situated close to the breast wall. In this case, the ultrasound transmitting/receiving 5 system consists of a single sagittal scanner. The sagittal scanner is a mechanical sector scanner with an ultrasound converter 6, which rotates around the axis 8 in direction of the rotation arrow 7. During the rotation procedure, sector-shaped, fan-like expanding transmitting/receiving directions result as depicted by the associated dotted lines. The transmitting/receiving directions which are essential for determining a coronal slice plane close to the breast wall are identified as $SE_1$ to $SE_n$.

Additionally, translational means are provided for moving the sagittal scanner about the object to be examined. The direction and manner of movement of the scanner about the object to be examined are described below.

Simultaneously with the sector scanning, the sector scanner is rotated slowly around the symmetry axis 9 extending through breast 1. In addition, the sagittal scanner travels in the direction of arrows 11 and 12 along the circular arc 10, depicted as dotted line. Based on these different forms of motion, a sector scanning of breast 1 results from the great number of different angle positions. FIG. 1 depicts two of these angle positions (180° in oppositely located positions) indicated on the left side of system 5 and drawn as a solid line, and on the right side of system 5 and drawn as a dotted line.

Figure 2:
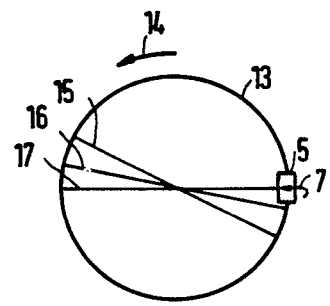
FIG. 2 depicts a schematic diagram to elucidate the sagittal slice procedure.

FIG. 2 illustrates a top view of the system of FIG. 1. Accordingly, the sagittal scanner is arranged on a ring 13, which rotates around axis 9 in the direction of arrow 14. The rotation or swivelling of the scanner in the direction of the rotation arrow 7 generates the sagittal slices, of which three are identified in FIG. 2 as 15, 16, and 17. The ring rotation frequency is much lower than the frequency with which the sagittal scanner is either swivelled or rotated. The rotation speed of the ring 13 which supports the sagittal scanner is approximately 0.1 Hz. However, the swivel or rotational frequency of the sagittal scanner is in the range of from 3 to 4 Hz.

Figure 3:
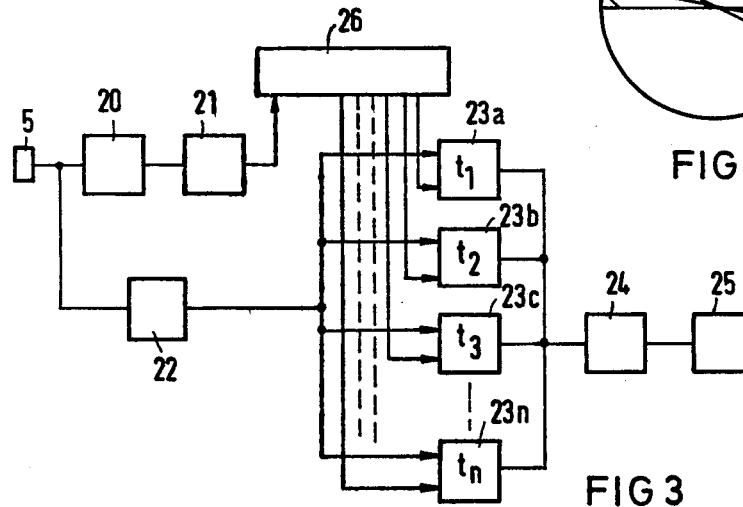
FIG. 3 illustrates a basic circuit diagram to be applied with this invention.

With the sample embodiment of FIG. 1, sagittal slices can be generated from a plurality of directions. Following an appropriate conversion in a computer, these sagittal slices can be displayed as sagittal computer tomography (CT) images. However, according to the present invention, the disclosed reconstruction process is capable of generating coronal slice images, especially of coronal slice images close to the breast wall. This is performed with a time gate circuit, as illustrated in FIG. 3. By applying this time gate circuit, signal data can be acquired section by section from the area sectors $A_1$ to $A_n$ in successive time intervals t1, t2, t3 ... tn, as depicted in FIG. 1. The sections $A_1$ to $A_n$ approximate closely the coronal slice plane close to the breast wall, which is indicated by arrow 4. Subsequent to an appropriate data conversion performed by a computer, a tomography image of a coronal plane close to the breast wall results. In addition, other parallel coronal slice planes can be provided by varying the time settings at the time gate circuit. The resulting scan sections can be combined to generate other parallel coronal slice planes. Of course, positions other than the illustrated position close to the breast wall of the scanning system 5 on circle 10 can be selected to determine the coronal slice plane close to the breast wall.

FIG. 3 depicts a basic diagram of a circuit for controlling the ultrasound transmitting/receiving system 5 of FIG. 1. Again, the sagittal scanner 5 is identified as such in this basic circuit diagram. As is known, the scanner is operated with a high frequency transmitter 20 including a clock generator 21. The ultrasound echo signals received from breast 1 during the rotation of the system are forwarded from a receiver amplifier 22 to a time gate circuit with time gates 23a to 23n. The time gates 23a to 23n will only allow echo signals to be forwarded section by section to the computer during the times $t_1$ to $t_n$ described in FIG. 1. From the data selected in this manner, the computer 24 calculates the approximated coronal slice close to the breast wall, which will be subsequently displayed on a display device 25. A central system configuration for the system has been identified with reference numeral 26. If other coronal slice planes are to be provided in addition to the coronal slice plane close to the breast wall, the times $t_1$ to $t_n$ in the time gate circuit only have to be changed in such a manner, that as a modification of FIG. 1, echo segments result, which lie in the approximated plane located parallel to the coronal plane which is close to the breast wall.

Figure 4:
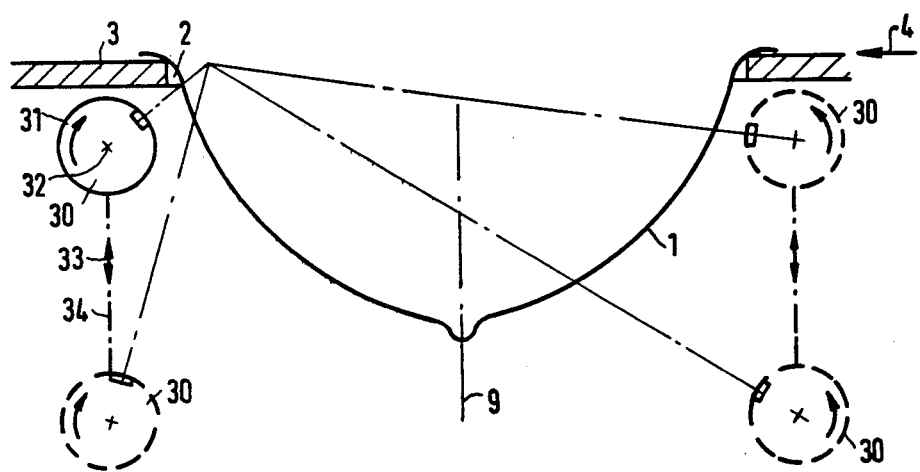
FIG. 4 shows a second sample embodiment of this invention.

FIG. 4 illustrates a modified sample embodiment. The device is similar insofar as a sagittal scanner 30 rotates again around the rotation axis in the direction of rotation arrow 31. However, in contrast to the sample embodiment of FIG. 1, this sagittal scanner 30 does not perform an additional circular arc 10 around the breast to be examined. Instead this sagittal scanner 30 travels in the direction of the double arrow 33 along the dotted line 34, which extends parallel to the rotation axis 9.

Figure 5:
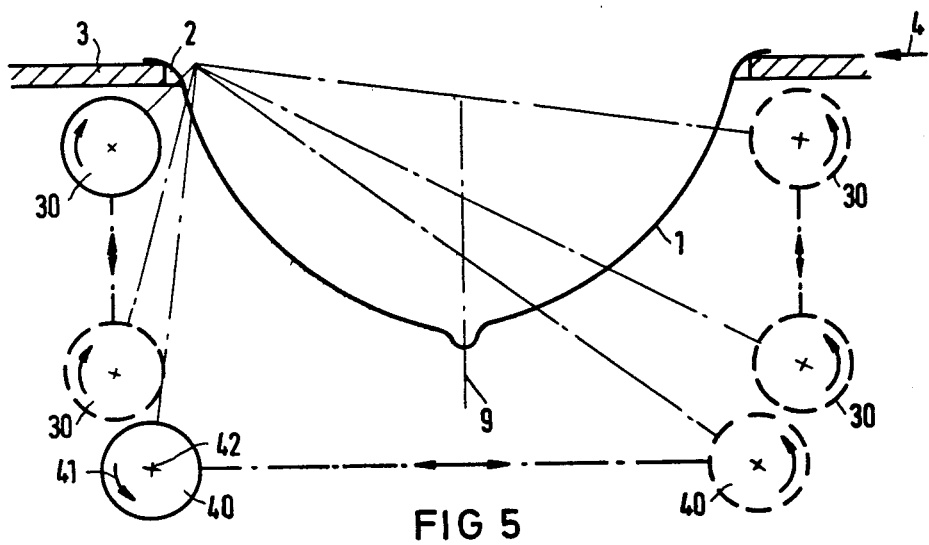
FIG. 5 shows a third sample embodiment of this invention.

FIG. 5 depicts a modified sample embodiment of FIG. 4 insofar as a second sagittal scanner 40 has been provided in addition to sagittal scanner 30. This second sagittal scanner 40 is capable of moving along the horizontal dotted line 42 in the direction of double arrow 41.

It is of course understood, that instead of a single sagittal scanner moving in a given direction, several sagittal scanners can be included in all embodiment examples to be distributed properly around the object to be examined. It is contemplated and should be understood that such an embodiment is also part of this invention. Equally, the invention enables application with scatter scan, wherein the same object point is sounded (irradiated) and/or addressed from different directions. For that purpose system 30 in FIG. 5 can be used for transmitting, while system 40 is used for receiving. If several systems have been distributed at the perimeter of the rotating ring 13 around the breast, one of these systems can be selected as transmitter and another as receiver.

There has thus been shown and described novel apparatus for ultrasound tomography which fulfills all the objects and advantages sought therefore. Many changes, modifications, variations and other uses and applications of the subject invention will, however, become apparent to those skilled in the art after considering this specification and the accompanying drawings which disclose preferred embodiments thereof.

All such changes, modifications, variations and other uses and applications which do not depart from the spirit and scope of the invention are deemed to be covered by the invention which is limited only by the claims which follow.

What is claimed is:

1. An ultrasound tomography device for line scanning an object to be examined from different angular directions which comprises in combination:
    a sagittal scanner having an ultrasound converter and being rotatably mounted so that the direction of said ultrasound converter results in a fan-like expanding transmitting/receiving direction which allows the acquisition of numerous line scan views of the object to be examined along the different ultrasound directions;
    translational means for moving said sagittal scanner about said object to be examined; said translational means being operative as to not interfere with said rotatability of said sagittal scanner;
    a time gate circuit for acquiring section by section signal data, during successive time intervals, from said ultrasound converter; and
    computer means for receiving said signal data and for combining said signal data in a data conversion routine for the generation of a tomography image of a coronal plane of the object to be examined.

2. The ultrasound tomography device according to claim 1, wherein said translational means are operable to move said sagittal scanner along a path which follows contours of said object to be examined at a predeterminable distance therefrom.

3. The device according to claim 1, wherein said translational means are operative to move said sagittal scanner along a circular arc situated in proximity to contours of said object to be examined.

4. The device according to claim 1, wherein said translational means are operative to move said sagittal scanner back and forth along an offset vertical straight line path which extends parallel to a symmetry axis extending through said object to be examined.

5. The device according to claim 1, wherein said translational means are operative to move said sagittal scanner back and forth along a horizontal straight line path which lies below said object to be examined and is essentially perpendicular to a symmetry axis extending through said object to be examined.

6. The device according to claim 1, further comprising at least one more rotatable sagittal scanner for scanning said object to be examined, and wherein said translational means are operative to move each sagittal scanner about said object to be examined without interference therebetween.

7. The device according to claims 1 or 6 wherein said sagittal scanner or scanners are mechanical sector scanners.

8. In an ultrasound tomography device which includes a sagittal scanner for line scanning an object from different directions and for providing sagittal scan images of said object the method of generating coronal slice images which comprises the steps of:
(a) rotating said sagittal scanner so that a fan-like expanding transmitting/receiving ultrasound direction results allowing the acquisition of numerous line scan views of an object to be examined;
(b) translating said sagittal scanner about said object to be examined so that said object is scanned by said scanner from a plurality of positions;
(c) acquiring, during successive time intervals, section by section signal data from said sagittal scanner, said section by section data being attributable to portions of said line scan views which lie along a coronal slice image plane; and
(d) combining said section by section signal data and generating a closely approximated tomography image of a coronal plane of the object to be examined.

* * * * *